United States Patent [19]

Madsen

[11] Patent Number: 5,389,657

[45] Date of Patent: Feb. 14, 1995

[54] METHOD FOR TREATING INFERTILITY

[75] Inventor: David C. Madsen, Libertyville, Ill.

[73] Assignee: Free Radical Sciences Corporation, Cambridge, Mass.

[21] Appl. No.: 12,006

[22] Filed: Feb. 1, 1993

[51] Int. Cl.$^6$ .......................................... A61K 31/425
[52] U.S. Cl. .................................................... 514/369
[58] Field of Search ........................................ 514/369

[56] References Cited

U.S. PATENT DOCUMENTS 4,665,082  5/1987  Meister et al. .................... 514/365
5,095,027  3/1992  Goldberg et al. .................. 514/369

OTHER PUBLICATIONS

Oeriu et al., Chemical Abstracts, CA74(3):13142a, 1970.
Calvin et al., Biosis, BA82:78019, 1986.
Slaweta et al., Chemical Abstracts, CA107(25)233949j; 1987.
Perreault et al., Biosis, BA85:62961, 1988.
Lassalle et al., Chemical Abstracts, CA117(15):148031r, 1992.
Bellin et al., *Purification of Glycosaminoglycans from Bovine Follicular Fluid*, Journal of Dairy Science, vol. 70, No. 9, pp. 1913–1919 (1987).
Calvin et al., *Estimation and Manipulation of Glutathione Levels in Prepuberal Mouse Ovaries and Ova:Relevance to Sperm Nucleus Transformation in the Fertilized Egg*, Gamete Research, vol. 14, pp. 265–275 (1986).
Gordon et al., *Applications of Micromanipulation to Human In Vitro Fertilization*, Journal of In Vitro Fertilization and Embryo Transfer, vol. 5, No. 2, pp. 57–60 (1988).
Perreault et al., *Importance of Glutathione in the Acquisition and Maintenance of Sperm Nuclear Decondensing Activity in Maturing Hamster Oocytes*, Developmental Biology, vol. 125, pp. 181–186 (1988).
Perrault et al., *The Timing of Hamster Sperm Nuclear Decondensation and Male Pronucleus, Formation is Related to Sperm Nuclear Bond Content*, Biology of Reproduction vol. 36, pp. 239–244 (1987).
Perreault et al., *The Role of Disulfide Bond Reducing during Mammalian Sperm Nuclear Decondensation in Vivo*, Developmental Biology, vol. 101, pp. 160,167 (1984).
Reyes et al., *Heparin and Glutathione: Physiological Decondensing Agents of Human Sperm Nuclei*, Gamete Research, vol. 23, pp. 39–47 (1989).
Zirkin et al., *In Vitro and in Vivo Studies in Mammalian Sperm Nuclear Condensation*, Gamete Research, vol. 11, pp. 349–365 (1985).
Shapiro, *The Control of Oxidant Stress at Fertilization*, Science, vol. 252, pp. 533–536 (1991).

Primary Examiner—Raymond J. Henley, III
Assistant Examiner—William R. A. Jarvis
Attorney, Agent, or Firm—Hill, Steadman & Simpson

[57] ABSTRACT

The present invention provides a method of treating infertility comprising administering to a female mammal having fertility problems a therapeutically effective amount of the glutathione stimulator L-2-oxothiazolidine-4-carboxylate or esters thereof.

12 Claims, No Drawings

METHOD FOR TREATING INFERTILITY

BACKGROUND OF THE INVENTION

The present invention relates generally to methods for treating infertility.

Infertility effects an estimated 1 in 5 couples in the United States. *The Merck Manual*, p. 1768 (16th Ed. 1992). About 40 percent of infertilities are due to male deficiency, 40-50 percent to female anatomic or hormonal defects, and the remainder to indeterminate factors. 17 *McGraw-Hill Encyclopedia of Science and Technology*, p. 417 (6th Ed. 1987).

Infertility refers to the inability to conceive during the course of normal sexual activity. However, a couple is generally not regarded as infertile until they have failed to conceive after one year of unprotected intercourse. Diagnosis and treatment of infertility requires a thorough assessment of both partners. *The Merck Manual*, p. 1768 (16th Ed. 1992).

The major factors leading to female infertility include: ovulatory dysfunction; abnormal tubular function; and cervical factors. In addition to these three factors, other undetermined factors also cause infertility. An undefined factor may be a compromised ability of the egg/embryo to produce a functioning fertilization envelope or withstand toxic effects of oxidants.

Immediately following fertilization in metazoans, including mammals, the external layer of the egg is rapidly modified to an effective barrier ("fertilization envelope"). The barrier protects the early embryo and prevents further entry of spermatozoa.

Shapiro, *The Control of Oxidant Stress at Fertilization*, Science, Vol. 252, pp. 533-36 (1991) discusses the production of a fertilization envelope in a sea urchin egg. Due to the large production of eggs, the sea urchin provides an excellent experimental system for studying molecular mechanisms of fertilization. In the sea urchin egg, a strong oxidant, probably hydrogen peroxide, is produced at or near the plasma membrane. An enzyme ("ovoperoxidase" in the invertebrate egg) uses the oxidant to initiate a cross-linking of proteins external to the egg surface. The cross-linking ultimately forms a protective fertilization envelope. The fertilization envelope persists for times that vary among species.

An oxidant, such as hydrogen peroxide, can cause significant damage if it enters the egg (either before or after fertilization) in significant amounts. The egg/embryo has biochemical mechanisms for handling oxidant which does defuse into it. In some animals, a family of modified amino acids ("ovothiols") consume hydrogen peroxide and are thereby oxidized to a disulfide. A reduced glutathione then reduces the ovothiol-disulfide to a thiolate. The ovothiol is then free to consume more oxidant.

The male deficiency most commonly responsible for infertility is a deficiency of sperm production in quantity or quality. 17 *McGraw-Hill Encyclopedia*, supra, at 417. The quantity and quality of sperm production depends, among other things, on the protection of the sperm cell membrane during and after ejaculation.

Similar to the potential peroxidation of the egg/embryo, oxidants within the male reproductive system can cause significant damage if they enter the sperm. Oxidants that diffuse into the sperm could be toxic. Thus, like the egg's biochemical mechanism for handling oxidants, semen in the male reproductive tract also has an effective defense mechanism. Glutathione plays a key role in this defense mechanism.

Glutathione plays a vital role in the protection of the sperm as well as the egg/embryo. Glutathione in its reduced state facilitates the consumption of oxidants which can cause significant damage if they enter the sperm or egg before or after fertilization.

The important role of glutathione will be compromised if the intracellular level of glutathione or the partitioning between the reduced and oxidized forms is abnormal. Such abnormality could ultimately be responsible for infertility, due to the compromised ability of the egg/embryo and sperm to produce respectively a functioning envelope and membrane or withstand toxic effects of oxidants.

Further, a compromised level of glutathione in the egg or uterine wall may also effect implantation of the fertilized egg. An inability to implant the fertilized egg could also cause infertility.

SUMMARY OF THE INVENTION

The present invention provides a method for treating infertility. Specifically, the present invention provides a method for treating infertility by increasing the intracellular synthesis of glutathione within the reproductive system. The method includes the step of administering to a mammal who is having difficulty conceiving a composition that stimulates the intracellular synthesis of glutathione.

Pursuant to the present invention, in an embodiment, the following compounds can be used as glutathione stimulators: glutathione; glutathione esters; L-2-oxothiazolidine-4-carboxylate; N-acetyl-cysteine; L-2-oxothiazolidine-4-carboxylate esters; and cysteine-rich protein.

In an embodiment, the intracellular glutathione stimulator is taken orally before and/or after intercourse.

In an embodiment, the intracellular stimulator is ingested by both partners.

In another embodiment, the intracellular glutathione stimulator is incorporated into a gel.

In yet another embodiment, the intracellular glutathione stimulator is present in a slow-release form implanted into the uterus. In a similar embodiment, the intracellular glutathione stimulator is present in a slow-release form implanted under the skin.

An advantage of the present invention is to provide a composition for treating infertility with substantially decreased side effects as compared to other fertility drugs. The intracellular glutathione stimulator of the present invention, especially L-2-oxothiazolidine-4-carboxylate, is less toxic than other fertility drugs.

Moreover, in contrast to other fertility drugs, only minimal risks of teratogenesis or other risks to the embryo/fetus are associated with the use of the present invention.

The decreased side effects and minimal risks associated with the present invention provide an ability to treat suspected infertility at earlier stages of diagnosis than with other fertility drugs. In other words, the present invention can be safely used if glutathione deficiency is suspected but not proven.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for treating infertility. In an embodiment, a method of treating infertility is provided comprising the step of administering to a suspected infertile mammal a therapeutically effective amount of an intracellular glutathione stimulator.

Increasing glutathione levels facilities the protection of the egg/embryo and sperm. Specifically, glutathione is involved in the antioxidant protection of the sperm and egg/embryo. Glutathione enzymes, such as glutathione peroxidase and glutathione reductase, provide a defense mechanism against sperm membrane and egg-/embryo envelope lipid per oxidation.

The glutathione stimulator may be selected from the group consisting of: L-2-oxothiazolidine-4-carboxylate; L-2-oxothiazolidine-4-carboxylate esters; glutathione; glutathione esters; cysteine-rich protein; and N-acetyl-cysteine.

As a protein, the intracellular glutathione stimulator should be at least 1.3 percent by weight cysteine. Therefore, as used herein, a "cysteine-rich protein" means a protein that is at least 1.3 percent by weight cysteine. This excludes the protein from being merely, casein, total milk product, or soy protein. On the other hand, whey (2.0 percent), egg white (2.5 percent), serum albumin (5.5 percent), and lactalbumin (5.8 percent) all have sufficient cysteine content, as well as mixtures including same.

Beside cysteine rich proteins, a number of compounds are known for stimulating the intracellular synthesis of glutathione. In addition to glutathione, pursuant to the present invention, other substrates that stimulate intracellular glutathione synthesis can be used. Some substrates include L-2-oxothiazolidine-4-carboxylate, other thiazolidine-4-carboxylate analogs and glutathione esters.

L-2-oxothiazolidine-4-carboxylate, in vivo, is subjected to the action of 5-oxo-L-prolinase in the presence of adenosine triphosphate to produce S-carboxyl cysteine. S-carboxyl cysteine is then decarboxylated to produce cysteine. Cysteine is then metabolized to provide glutathione. See, U.S. Pat. Nos.: 4,355,210; 4,434,158; 4,438,124; 4,665,082; and 4,647,571 the disclosures of which are incorporated herein by reference.

Esters of 2-oxothiazolidine-4-carboxylate are disclosed in U.S. patent application Ser. No. 07/932,761 entitled: "METHOD FOR STIMULATING INTRACELLULAR SYNTHESIS OF GLUTATHIONE USING ESTERS OF L-2-OXOTHIAZOLIDINE-4-CARBOXYLATE," filed in the name of W. Bruce Rowe and assigned to the assignee of the instant patent application. The disclosure of that patent application is hereby incorporated by reference.

The ester of L-2-oxothiazolidine-4-carboxylate is preferably an alkyl group of 1 to 10 carbon atoms. Preferably, the ester is chosen from a saturated straight alkyl group such as methyl, ethyl, propyl, butyl, pentyl, hexyl, heptyl, octyl, nonyl, or decyl and a saturated branched alkyl group such as isopropyl, isobutyl, sec-butyl, tert-butyl, or isopenyl. Although methyl, ethyl, propyl, isopropyl, butyl, and isobutyl are especially useful for medical applications, at this time, ethyl ester is preferred.

As previously stated, the non-cysteine substrate can include a glutathione ester. For example, the compound can have the structure:

wherein R is an alkyl group containing 1 to 10 carbon atoms. Preferably, the methyl, ethyl or isopropyl glutathione esters are used. It is also preferred to use glutathione short chain acetyl ester. Glutathione esters are disclosed in U.S. Pat. No. 4,784,685, the disclosure of which is incorporated herein by reference.

Additionally, N-acetyl-cysteine can be utilized pursuant to the present invention to stimulate intracellular synthesis of glutathione.

The composition of the present invention can be administered either parenterally or enterally.

By way of example, the composition of the present invention as a parenteral product can include a solution of 1% to 12% (weight:volume) L-2-oxothiazolidine-4-carboxylate in aqueous solution, with a suitable buffer, such as 5 mM phosphate buffer. Other glutathione stimulators can be prepared in vehicles appropriate to their physicochemial properties and stability requirements.

The parenteral product would be administered preferably while the patient is sleeping, to minimize discomfort and inconvenience. However, devices exist that permit daily continuous or intermittent infusion for periods of up to many months. The composition would be administered daily for as long as the managing physician decides. This period would normally last as long as it takes to effect a change in measurable parameters of fertility or until conception occurs. For example, daily infusions of 12 hours duration (during evenings) could be carried out using a concentration and infusion rate to achieve a total dose of 5.0 grams per day. The regimen continues until end points are achieved.

In an embodiment, the composition is administered as part of a parenteral nutrition regimen.

When administered enterally, the composition can be taken orally before and/or after intercourse. Enteral composition can be provided as tablet, capsule, or incorporated into foods such as juices or shakes. The amount to be ingested daily will depend on patient response. Three daily doses of three capsules, 0.5 grams per capsule achieves an empirical dose of 4.5 grams per day. Preferably, this dosage continues for not less than two weeks, and more preferably for months.

The composition of the present invention can also be administered through gynecological applications. For instance, in one embodiment, the composition is incorporated into a gel. Such gel can be used either as a douche or a lubricant for copulation. Still further, the composition of the present invention can be incorporated into a gel for direct application to the external aspect of the testicles.

In another embodiment, the composition is in a slow-release form implanted into the uterus, as are some birth-control devices. Likewise, in an embodiment, the composition of the present invention is in a slow-release form implanted under the skin, as is done with some forms of birth control.

If desired, the compositions of the present invention can be administered with other fertility agents.

By way of example, and not limitation, a contemplative example of the present invention will now be given.

CONTEMPLATED EXAMPLE

A couple had tried unsuccessfully for over three years to conceive. It was found that the male had an abnormal sperm profile: the concentration of the sperm was significantly lower than normal, and a higher than normal percentage of atypical forms of sperm existed. The male was started on enteral L-2-oxothiazolidine-4-carboxylate, total dose of 4.5 grams.

After eight weeks, the concentration of sperm as well as the number of atypical forms had significantly improved towards normal. The therapy was continued. During this time the couple also used lubricating gels and daily vaginal douches containing L-2-oxothiazolidine-4-carboxylate. Conception was achieved seven months after the start of the treatment.

Understandably, various changes and modifications can be made to the presently preferred embodiments described herein and will be apparent to those skilled in the art. Such changes and modifications can be made without departing from the spirit and scope of the present invention and without diminishing its attendant advantages. Therefore, the appended claims are intended to cover such changes and modifications.

I claim:

1. A method for treating infertility comprising the step of administering to a female patient having fertility problems a therapeutically effective amount of an intracellular glutathione stimulator chosen from the group consisting of: L-2-oxothiazolidine-4-carboxylate; and L-2-oxothiazolidine-4-carboxylate esters to provide a defense mechanism against egg/embryo envelope lipid per oxidation.

2. The method of claim 1 wherein the intracellular glutathione stimulator is administered parenterally.

3. The method of claim 1 wherein the intracellular glutathione stimulator is administered enterally.

4. The method of claim 1 wherein the intracellular glutathione stimulator is incorporated into a gel.

5. The method of claim 4 wherein the gel is a lubricating gel.

6. The method of claim 4 wherein the gel is used as a vaginal douche.

7. The method of claim 1 wherein the intracellular glutathione stimulator is in a slow-release form implanted into the uterus.

8. The method of claim 1 wherein the intracellular glutathione stimulator is in a slow-release form implanted under the skin.

9. The method of claim 1 wherein the intracellular glutathione is administered before intercourse.

10. The method of claim 1 wherein the intracellular glutathione is administered after intercourse.

11. The method of claim 1 wherein the intracellular glutathione stimulator is part of a complete nutritional formulation for providing nutritional requirements to the mammal.

12. The method of claim 1 including the step of administering an additional fertility agent.

* * * * *